United States Patent [19]
Yamamoto et al.

[11] Patent Number: 4,874,787
[45] Date of Patent: Oct. 17, 1989

[54] INSECTICIDAL ARTICLE FOR ELECTRIC FUMIGATOR

[75] Inventors: Shinobu Yamamoto; Kunihiro Okada; Satoshi Ohi, all of Hiroshima; Shiro Oyama, Urawa; Yasuharu Takei, Hiroshima, all of Japan

[73] Assignee: Sumitomo Chemical Company, Limited, Osaka, Japan

[21] Appl. No.: 83,249

[22] Filed: Aug. 10, 1987

[30] Foreign Application Priority Data

Aug. 15, 1986 [JP] Japan ................................ 61-191527

[51] Int. Cl.⁴ ...................... A61K 31/05; A01N 65/00
[52] U.S. Cl. .............................. 514/531.125; 514/65; 514/67; 424/403
[58] Field of Search .................. 424/403; 514/531, 65, 514/67

[56] References Cited

U.S. PATENT DOCUMENTS

| 3,906,089 | 9/1975 | Okuno et al. | 514/417 |
| 3,934,023 | 1/1976 | Okunu et al. | 514/531 |
| 4,515,808 | 5/1985 | Elliott et al. | 514/531 |

FOREIGN PATENT DOCUMENTS

| 0148625 | 7/1985 | European Pat. Off. |
| 52-45768 | 11/1977 | Japan . |
| 53-121927 | 10/1978 | Japan . |
| 54-98324 | 3/1979 | Japan . |
| 55-41201 | 10/1980 | Japan . |
| 2002635 | 2/1979 | United Kingdom . |
| 1587396 | 4/1981 | United Kingdom . |
| 2130883 | 6/1984 | United Kingdom . |
| 2180751 | 4/1987 | United Kingdom . |

OTHER PUBLICATIONS

Tsuda et al., "Studies Pyrethroidal Compounds Part II", Botyū-Kagaku, vol. 37 II, pp. 48–56 (1972).
Hayashi, "The Insecticidal Activity of Synthetic Pyrethroids", Botyū-Kagaku, vol. 37 II, pp. 67–81 (1972).

Primary Examiner—William R. Dixon, Jr.
Assistant Examiner—Anthony J. Green
Attorney, Agent, or Firm—Stevens, Davis, Miller & Mosher

[57] ABSTRACT

An insecticidal composition for electric fumigator consisting essentially of:
(A) an insecticidally effective amount of a preparation comprising 2-methyl-4-oxo-3-(2-propynyl)cyclopent-2-enyl-chrysanthemate and a synergist, wherein the weight ratio of said synergist to said chrysanthemate ranges from ½ to 8, and
(B) a porous mat suitable for use on an insecticidal mat, said porous mat being impregnated with said preparation. This composition has both a lower content of an insecticidal active ingredient than ever and the capability of exhibiting a sufficient insecticidal activity over a long period of time.

6 Claims, No Drawings

INSECTICIDAL ARTICLE FOR ELECTRIC FUMIGATOR

The present invention relates to an insecticidal article for electric fumigator used for destroying insects, e.g. mosquitos, houseflies etc. More particularly, this relates to an insecticidal article for an insecticidal mat used for electric fumigator containing a small amount of an insecticidally active ingredient, which article exhibits a sufficient insecticidal activity over a long period of time when it is heated by means of an electric heater or the like to fumigate the said active ingredients in the air.

Up to this time, various apparatuses for controlling injurious insects are used in homes. Such apparatuses include so-called mosquito coil (a mosquito repellant incense), oily insecticide, aerosol, electric fumigator and recently-developed portable mosquito destroyer for camping or out-door labor utilizing the oxidation of methanol with catalyst. Among these, electric fumigator is widely used. A method for controlling insects by heat fumigation is as follows:

A mat made of pulp, asbestos, inorganic porous substances, porous synthetic resin or the like is impregnated (dipped and dropped) and/or coated with insecticidal pyrethroid preparation. This mat is then heated at about 120°–200° C. by an electric heater or the like to effectively fumigate a certain amount of an insecticidally active ingredient over a long period of time.

The object of this method is to exhibit the insecticidal activity over a long period of time by fumigating the active ingredient constantly by heat. The insecticidal preparation comprises an insecticide capable of heat fumigation such as Pynamin Forte ® [dl-3-allyl-2-methylcyclopent-2-en-4-on-1-yl-d-cis.trans-cyrysanthemate (a trade mark of Sumitomo Chemical Co., Ltd.)], a proper amount of fumigation regulator, an antioxidant, perfume, dyestuff and the like. These heat fumigating insecticidal mats are impregnated with more than 40 mg of this preparation per mat to exhibit a sufficient insecticidal activity.

Since Pynamin Forte, which generally is used as an insecticide in the heat fumigating insecticidal mat, has a low thermal stability, i.e. an easily decomposing property, an antioxidant is added thereto to suppress the thermal decomposition. Also it has so high vaporizability that it is fumigated off in a short time, so that an antioxidant, synergist and/or an organic compound having high boiling points are added to control the fumigation. Pynamin Forte shows a relatively high knock-down effect, however, it does low mortality effect compared with the other pyrethroid insecticides.

Until now, there has been a lot of research aimed at increasing the mortality effect of ordinary temperature-contact type preparations such as oily or powdery preparations (formulations), emulsions or aerosols. As a result, it has been clearly shown that the addition of so-called synergist to pyrethroid insecticide improves the insecticidal activity. However, it is greatly influenced by the type of insecticidally active ingredient or synergist, the combination thereof, the form of insecticide or the species of injurious insects. In some cases, there occurs no improvement on the insecticidal activity even when the synergist is added. As to the heat fumigating preparation, the similar effect is generally believed to be given. However, detailed reports about said preparation are surprisingly few. Among them, there is a study about the mosquito coil, reporting that the trend of variation of the insecticidal activity in the mosquito coil differs from those in the other formulations ("On the Insecticidal Activity of Synthetic Pyrethroids", BOTYU-KAGAKU, (Insect Control Science), vol. 37, II 67–81 (1972)). The present inventors have also examined the preparations for heat fumigating insecticidal mat to obtain the results that the trend of variation of the insecticidal activity by them is far from that by ordinary temperature-contact type preparation. The addition of synergist, depending on the type or the amount, sometimes gives no improvement, or sometimes gives even deterioration on the activity by regulating the fumigation.

Above all, the health of consumers becomes more and more important nowadays. Therefore, a heat fumigating insecticidal mat having a low content of insecticidal active ingredient from the viewpoint of the security i.e. low toxicity and environmental pollution is desired. That is also advantageous in economy since the lowering the content of insecticidal active ingredient used can reduce the manufacturing cost.

However, as mentioned above, the effect of synergist to the insecticidal active ingredient has not been clear enough in the preparation used in the heat fumigating insecticidal mat. The addition of synergist does not always improve the insecticidal activity, or in some cases, on the contrary it reduces the insecticidal activity depending on the type or amount of synergist. Needless to say, there has not been obtained yet a heat fumigating insecticidal mat having both the lower content of insecticidal active ingredient used than ever and the capacity of exhibiting the insecticidal activity over a long period of time.

Accordingly, an object of the present invention is to provide an insecticidal article for electric fumigator used for destroying insects, e.g. mosquitos, houseflies etc., said article having a low content of the insecticidal active ingredient in an insecticidal mat, being able to constantly fumigate the insecticidal active ingredient and synergist in the air to exhibit a sufficient insecticidal activity over a long period of time.

It is found that this object is attained by the article of the present invention consisting essentially of the preparation comprising a specific insecticidal active ingredient, a specific portion of a specific synergist and a porous mat, said mat being impregnated and/or coated with said preparation.

An insecticidal article for electric fumigator of the present invention consisting essentially of:

(A) an insecticidally effective amount of a preparation comprising 2-methyl-4-oxo-3-(2-propynyl)cyclopent-2-enyl-chrysanthemate (hereinafter referred to as the PA) and a synergist, wherein the weight ratio of said synergist to the PA ranges from ½ to 8, and (B) a porous mat, said porous mat being impregnated with said preparation.

According to the present invention, there is provided a remarkably high synergistic effect that the fumigation ratio of synergist to insecticidal active ingredient is maintained on a high level over a long period of time, hence a sufficient insecticidal activity continues to be exhibited over a long period of time though small amount of the PA is used.

The insecticidal mat of the present invention contains from 5 to 20 mg of the PA mentioned above, while the conventional mats usually contain about 2-fold amounts of insecticidal active ingredient. Thus, the mat of this invention, using smaller amount of insecticidal active ingredient, has various advantages such as low environmental pollution, high safety and low manufacturing cost.

As the synergist, usable are α-[2-(2-butoxyethoxy)ethoxy]-4,5-methylenedioxy-2-propyltoluene (hereinafter referred to as piperonyl butoxide), octachlorodipropyl ether (hereinafter referred to as S-421) and N-(2-ethylhexyl)-bicyclo-[2,2,1]-hept-5-en-2,3-dicarboxyimide (hereinafter referred to as MGK-264), more preferably piperonyl butoxide.

The synergistic effect is scarecely revealed in the conventional insecticidal mat using Pynamin Forte. The reason for this is considered as follows:

First, the vapor pressure of Pynamin Forte differs from those of conventionally used synergists. Thus, synergists are fumigated so rapidly or so slowly compared with Pynamin Forte that it fails to exhibit the synergistic effect. Second, because of the rapid fumigation of Pynamin Forte, it is relatively difficult to control the fumigation rate of Pynamin Forte. In other words, it is difficult to fumigate the sufficient amount of synergist to make the synergistic effect exhibit over a long period of time. And above all, it is very difficult to select the proper type or portion of synergist accordingly. Therefore, under such situation, it is almost impossible to obtain an insecticidal mat having a sufficient insecticidal activity with a low content of the insecticidal active ingredient.

The PA used in the preparation of the present invention, when compared with Pynamin Forte, has excellent properties such as low fumigation rate and high insecticidal activity so that it can be practically used within the wide range of the content, especially in low content.

However, even though the PA has above-mentioned excellent properties, it cannot exhibit a sufficient insecticidal activity when the content becomes too low. In such a case, a synergist may be added thereto to exhibit the synergistic effect so as to attain a high insecticidal activity.

In general, it is necessary to enhance the fumigation ratio of synergist to insecticidal active ingredient to improve the insecticidal activity by utilizing sufficient synergistic effect. The present inventors have found that an article capable of exhibiting the excellent insecticidal activity over a long period of time is produced from the high fumigation ratio of synergist to insecticidal active ingredient by using the above-mentioned PA and specific synergist in a specific content ratio.

The PA has geometric isomers derived from acid moiety and optical isomers derived from the assymmetric carbon atoms of acid moiety and alcohol moiety. In the present invention, these isomers can be used alone or in admixture thereof.

The content of the PA used is within the range from 5 to 20 mg per mat in the present invention. One reason for this is to meet the object of the present invention to lower the content of the PA used. The other is that it is difficult to obtain a high fumigation ratio of synergist to insecticidal active ingredient when the PA is used in high content. Because in such a case, there is a difficulty in controlling the fumigation ratios of the PA and synergist, which fumigation ratios are often repressed. The PA content defined above is based on a mat having 22 mm in width, 35 mm in length and 2 mm in thickness, so that when a mat of different size is used, the PA content may be determined according to as described above.

The mat can be used at a thickness ranging from 1 to 3 mm, preferably 1.5 to 2.5 mm.

The weight ratio of synergist to the PA ranges from ½ to 8. When the ratio is less than ½, the fumigation ratio of synergist to the PA becomes so low that a sufficient synergistic effect is not produced. On the contrary, when the ratio exceeds 8, the mortality of insects only shows a slight improvement to the case where the PA is used alone. Thus, the maximum mortality can be expected in value within the range from around 1 to 4 of the weight ratio.

In addition to the PA and synergist, known additives such as an antioxidant, repellant, fumigation regulator, perfume or dyestuff can be added to the preparation of the present invention. Since the chrysanthemates generally lack stability to heat, light and oxidation, there can be added to improve the stability a proper amount of antioxidant such as 2,6-di-tert-butyl-4-methylphenol (BHT), 3-tert-butyl-4-hydroxyanisole (BHA), 2,2′-methylene-bis(4-ethyl-6-tert-butylphenol), 2,2′-methylene-bis(4-methyl-6-tert-butylphenol), 4,4′-butylidene-bis(5-methyl-6-tert-butylphenol), 4,4′-methylenebis(2-methyl-6-tert-butylphenol), 4,4′-thio-bis(3-methyl-6-tert-butylphenol), 4,4′-methylene-bis(2,6-di-tertbutylphenol), stearyl-β-(3,5-di-tert-butyl-4-hydroxyphenol)-propionate, 1,3,5-trimethyl-2,4,6-tris(3,5-di-tert-butyl-4-hydroxybenzylbenzene), 1,1,3-tris(2-methyl-4-hydroxy-5-tert-butyl)butane, tetrakis[methylene(3,5-di-tert-butyl-4-hydroxycinnamate)]methane, dilauryl thiodipropionate and distearyl thiodipropionate, or U.V. absorber derived from benzophenone, triazole, salicylate compounds or the like.

As to the PA, it is necessary to add one or more stabilizers such as antioxidants or U.V. absorbers as described above.

The insecticidal mat of the present invention can be manufactured by impregnating and/or coating on a porous substance such as pulp, asbestos, porous synthetic resin, porous inorganic powder, glass fiber, cloth, mineral powder, porous porcelain material or the like with above-mentioned preparation. One example of porous mat used in the present invention is a mat consisting of 50% of cotton fiber and 50% of pulp fiber. It is preferable to use natural fibers for the mat from the viewpoint of the absorptivity and maintenance of an insecticidal active ingredient. This manufacture can be conducted by either volatile solvent method or method unutilizing volatile solvent. The volatile solvent method is carried out as follows:

The insecticidal preparation is dissolved in an volatile organic solvent. Necessary amount of the preparation is given to a mat by dipping the mat in this solution or by making this solution fall in drops on the mat. Then the mat is dried by removing volatile solvent and packed. However, method unutilizing volatile solvent is preferable because volatile solvent method has disadvantages such as environmental pollution and danger of fire by using a lot of volatile organic solvent and dryer thereof. With the method unutilizing volatile solvent, the preparation without organic solvent is made fall in drops onto the mat followed by the packaging thereof. In 2 or 3 days, at ordinally temperature (ca. 20°–25° C.), the preparation diffuses uniformly over the mat. The PA used in the present invention is a liquid at room temperature (ca. 20°–25° C.), so that the method unutilizing volatile solvent can be advantageously utilized.

The following examples are designed to further illustrate the practice of the present invention and are not to be considered unduly limitative of the scope of the present invention.

EXAMPLE 1

Porous mats (cotton fiber: 50%, pulp fiber: 50%) of 35 mm in length, 22 mm in width and 2 mm in thickness were impregnated with different preparation consisting of 5, 10, 20, 30 or 40 mg of (S)-2-methyl-4-oxo-3-(2-propynyl)cyclopent-2-enyl(1R)-cis.trans-chrysanthemate (hereinafter referred to as Prallethrin), 40 mg of piperonyl butoxide, 15 mg of BHT and 0.5 mg of a dyestuff to prepare the test insecticidal mats. For the comparison with them, commercially available mat A containing 40 mg of Pynamin Forte and 40 mg of piperonyl butoxide was also tested (22 mm in width, 35 mm in length and 2.8 mm in thickness). These mats were subjected to fumigation on an electric heater at 165° C for 12 hours successively. The fumigation rates of synergist and insecticidal active ingredient at the 2 hour interval were determined from the quantitative analyses of Prallethrin, Pynamin Forte and piperonyl butoxide. The results are shown in Table 1.

The fumigated amount of the insecticidal active ingredients and synergist were determined as follows:

Vaporized samples were trapped in succession at the interval of 2 hours by silica gel-packed columns and extracted with chloroform; the extracts were then quantitatively analyzed by gas chromatography.

The fumigation ratios were calculated according to the formula below:

Fumigation ratio = (fumigated amount of synergist)/(fumigated amount of insecticidal active ingredient)

TABLE 1

| passage of time (hr) | fumigation ratio Prallethrin content (mg/mat) | | | | | Commercially available mat A |
|---|---|---|---|---|---|---|
| | 5 | 10 | 20 | 30 | 40 | |
| 0–2 | 1.68 | 1.24 | 1.03 | 0.66 | 0.23 | 0.12 |
| 2–4 | 2.03 | 1.29 | 1.29 | 0.74 | 0.34 | 0.17 |
| 4–6 | 2.81 | 1.45 | 1.33 | 0.88 | 0.41 | 0.22 |
| 6–8 | 4.27 | 1.58 | 1.40 | 0.90 | 0.55 | 0.29 |
| 8–10 | 5.35 | 1.70 | 1.54 | 1.06 | 0.61 | 0.37 |
| 10–12 | 6.80 | 2.37 | 1.67 | 1.24 | 0.73 | 0.48 |

As is clear from the results above, the high fumigation ratios are obtained when the mats contain 5–20 mg of Prallethrin per mat. It gave about decuple values compared with the value in the case where the commercially available mat A was used. Therefore, in the present invention, high synergistic effects are expected. This is also shown in the following Examples.

EXAMPLE 2

The test mats were prepared by impregnating porous mats (cotton fiber: 50%, pulp fiber: 50%) with the preparations consisting of 5, 10, 20, 30 and 40 mg of Prallethrin, 20 mg of piperonyl butoxide, 10 mg of 2,2'-methylene-bis(4-ethyl-6-tert-butylphenol) as an antioxidant and 0.5 mg of a dyestuff. A test mat was also prepared by impregnating the mat with a preparation (blank) consisting of the same components as above except piperonyl butoxide.

In a cylinder of 20 cm in bore and 45 cm in height, 20 female adult mosquitos (Culex pipiens) were released. In this cylinder, an electric fumigator having a test mat on, of which mat had been fumigated by the heater at 165° C., was placed for 30 seconds. Then the knocked-down mosquitos were put out, and the number of dead mosquitos were counted at after 24 hours. The procedure was repeated five times. The mortality is defined as the value obtained by dividing the total number of dead mosquitos by total number of released mosquitos, and the mortality ratio is calculated as follows:

Mortaliy ratio = (mortality in the case where the synergist-containing mat is used)/(mortality in the case where the blank mat is used)

The results are shown in Table 2.

TABLE 2

| passage of time (hr) | mortality ratio Prallethrin content (mg/mat) | | | | |
|---|---|---|---|---|---|
| | 5 | 10 | 20 | 30 | 40 |
| 0–2 | 1.54 | 1.62 | 1.50 | 1.25 | 1.16 |
| 2–4 | 2.34 | 2.11 | 1.59 | 1.36 | 1.06 |
| 4–6 | 2.45 | 2.34 | 1.78 | 1.38 | 1.03 |
| 6–8 | 3.16 | 2.11 | 1.92 | 1.40 | 1.13 |
| 8–10 | 3.73 | 3.14 | 1.64 | 1.35 | 1.16 |
| 10–12 | 4.12 | 3.08 | 2.03 | 1.48 | 1.14 |

From the above results, it is observed that within the range where the contents of Prallethrin were relatively low, high mortality ratios, i.e. high synergistic effects were obtained. It is also expected that the mortality ratios became less than 1 and no synergistic effect is exhibited when the synergist content is less than ½ of Prallethrin content.

EXAMPLE 3

Test mats were prepared by impregnating the mats (cotton fiber: 50%, pulp fiber: 50%) having the same size as above with 10 mg of Prallethrin, 0, 10, 20, 40, 60 or 80 mg of piperonyl butoxide, 10 mg of BHT and 1 mg of a dyestuff.

The mortality test was carried out in the same manner as in Example 2 to clarify the effect of synergist. The results are shown in Table 3.

TABLE 3

| passage of time (hr) | mortality ratio synergist content (mg/mat) | | | | | |
|---|---|---|---|---|---|---|
| | 0 blank | 10 | 20 | 40 | 60 | 80 |
| 0–2 | 1.00 | 1.93 | 1.78 | 1.73 | 1.54 | 1.38 |
| 2–4 | 1.00 | 2.03 | 2.18 | 1.70 | 1.73 | 1.46 |
| 4–6 | 1.00 | 2.30 | 2.32 | 2.22 | 1.96 | 1.52 |
| 6–8 | 1.00 | 2.21 | 2.58 | 2.38 | 2.00 | 1.66 |
| 8–10 | 1.00 | 2.10 | 2.22 | 2.10 | 1.83 | 1.74 |
| 10–12 | 1.00 | 2.14 | 2.25 | 2.05 | 1.67 | 1.56 |

From the results above, it is evident that remarkably high synergistic effects were obtained when the synergist contents were less than 8-times of Prallethrin content.

EXAMPLE 4

A test mat was prepared by making fall in drops of the preparation consisting of 10 mg of Prallethrin, 30 mg of piperonyl butoxide, 20 mg of BHT and 1 mg of a dyestuff on the mat (cotton fiber: 50%, pulp fiber: 50%) having the same size as above. The other test mat (blank) was prepared in the same manner as above except that piperonyl butoxide was not contained in the preparation.

In the chamber having 28 $m^3$, the fumigations were carried out by using the each test mat for 12 hours successively at heating temperature of 165° C. Then, 100 female adult mosquitos were released in this chamber at intervals as shown in the Table 4. Two hours later, the knocked-down mosquitos were put out and the numbers of dead mosquitos were counted at after 24 hours. The mortality is defined as same as above. The results are shown in Table 4.

For the comparison with this, there were also tested the commercially available mat B containing 40 mg of Pynamin Forte and 30 mg of piperonyl butoxide and the same one containing the same components except piperonyl butoxide (both having the same size as 22 mm in width, 35 mm in length and 2.8 mm in thickness). The mortalities and mortality ratios of commercially available mat B to its blank were determined in the same manner as above. The results are shown in Table 4.

TABLE 4

| passage of time (hr) | mortality ratio | |
|---|---|---|
| | the present composition (used Prallethrin) | commercially available mat B (used Pynamin Forte) |
| 0-2 | 1.52 | 1.09 |
| 3-5 | 1.85 | 1.04 |
| 7-9 | 2.25 | 0.97 |
| 10-12 | 3.10 | 0.93 |

From the results above, it is clear that there was no synergistic effect by piperonyl butoxide when Pynamin Forte was used. On the contrary, remarkably high synergistic effect was produced when the insecticidal active ingredient of the present invention was used.

What is claimed is:

1. An insecticidal article for electric fumigator consisting essentially of:
   (a) a preparation comprising 2-methyl-4-oxo-3-(2-propynyl) cyclopent-2-enyl-chrysanthemate and a synergist selected from the group consisting of α-[2-(2-butoxyethoxy)ethoxy]-4,5-methylenedioxy-2-propyltoluene, octachlorodipropyl ether and N-(2-ethylhexyl)-bicyclo-[2,2,1]-hept-5-en-2,3-dicarboxyimide, wherein the weight ratio of said synergist to said chrysanthemate ranges from ½ to 8, and
   (b) a porous mat suitable for use on an insecticidal mat, said porous mat being impregnated with said preparation.

2. An insecticidal article according to claim 1, wherein the synergist is -α-[2-(2-butoxyethoxy)ethoxy]-4,5-methylenedioxy-2-propyltoluene.

3. An insecticidal article according to claim 1, wherein the content of synergist ranges from 1 to 4 parts by weight per part of 2-methyl-4-oxo-3-(2-propynyl)-cyclopent-2-enyl-chrysanthemate.

4. An insecticidal article according to claim 1, wherein the amount of 2-methyl-4-oxo-3-(2-propynyl)-cyclopent-2-enyl-chrysanthemate ranges from 5 to 20 mg per mat.

5. An insecticidal article according to claim 1, wherein the chrysanthemate is (S)-2-methyl-4-oxo-3-(2-propynyl) cyclopent-2-enyl(1R)-cis.trans-chrysanthemate.

6. A preparation comprising 2-methyl-4-oxo-3-(2-propynyl) cyclopent-2-enyl-chrysanthemate and a synergist selected from the group consisting of α-[2-(2-butoxyethoxy)ethoxy]-4,5-methylenedioxy-2-propyltoluene, octachlorodipropyl ether and N-(2-ethylhexyl)-bicyclo-[2,2,1]-hept-5-en-2,3-dicarboxyimide, wherein the weight ratio of said synergist to said chrysanthemate ranges from ½ to 8.

* * * * *